United States Patent [19]

Dahlquist

[11] Patent Number: 4,879,471

[45] Date of Patent: Nov. 7, 1989

[54] RAPID-SCANNING INFRARED SENSOR

[75] Inventor: John A. Dahlquist, Palo Alto, Calif.

[73] Assignee: Measurex Corporation, Cupertino, Calif.

[21] Appl. No.: 29,805

[22] Filed: Mar. 25, 1987

[51] Int. Cl.$^4$ .................. G01J 1/00; G01N 21/81
[52] U.S. Cl. ................. 250/359.1; 250/339; 250/341; 250/347; 250/563; 356/431
[58] Field of Search .............. 250/339, 341, 347, 349, 250/358.1, 359.1, 562, 563, 571, 572

[56] References Cited

U.S. PATENT DOCUMENTS

| | | | |
|---|---|---|---|
| 3,373,869 | 3/1968 | Burson, Jr. | 250/347 |
| 3,532,887 | 10/1970 | Clark | 250/347 |
| 3,754,146 | 8/1973 | Chow | 250/563 |
| 3,783,296 | 1/1974 | Blevins | 250/572 |
| 4,013,367 | 3/1977 | Nagao | 250/572 |
| 4,093,866 | 6/1978 | Kasdam | 250/563 |
| 4,465,929 | 8/1984 | Edgar | 250/353 |
| 4,631,408 | 12/1986 | Zelmanovic | 250/341 |

Primary Examiner—Eugene R. LaRoche
Assistant Examiner—Nathan W. McCutcheon
Attorney, Agent, or Firm—Burns, Doane, Swecker & Mathis

[57] ABSTRACT

A scanning system and method for optically measuring parameters such as dry basis weight, basis weight and moisture content of fibrous sheets during manufacture. The system includes a first track that extends generally parallel to one face of a traveling web in the cross direction; a stationary light source arranged to direct collimated light generally parallel to the first track; a first reflector that travels along the first track and focuses the collimated light against the adjacent face of the web; a second track that extends parallel to the first track adjacent the opposite face of the web; a second reflector that travels along the second track and collects and collimates rays that are transmitted through the web; and stationary light detectors that detect the intensity of the collected rays at least at two selected ranges of wavelengths to measure the absorption properties of the traveling web at selected locations.

23 Claims, 2 Drawing Sheets

RAPID-SCANNING INFRARED SENSOR

BACKGROUND OF THE INVENTION

1. Field of the Invention

The present invention generally relates to a system and method for measuring properties of traveling webs of fibrous sheet material during manufacture and, more particularly, to a system and method for providing measurements of fibrous sheet materials using infrared measuring techniques.

2. State of the Art

In the manufacture of fibrous sheet materials such as paper and cardboard, important parameters for process control and product quality include basis weight and moisture content. Basis weight is defined as the weight per unit area of sheet material and is typically stated in units of grams per square meter. Dry basis weight refers to weight per unit area excluding moisture and, for paper products, is equivalent to the weight of dry material, primarily fibers, comprising a given area of a sheet. Moisture content refers to the amount of moisture per unit area of a sheet. These parameters are related by the fact that, for a given area of a sheet, basis weight minus moisture content equals dry basis weight.

It is well known that basis weight and moisture can be determined by laboratory physical tests. However, laboratory tests have several inherent drawbacks. One shortcoming is that substantial periods of time are required for sample acquisition and analysis. During those periods, production conditions may change sufficiently that the laboratory tests results, when available, are no longer representative of current manufacturing or product conditions. Another drawback of laboratory tests is that samples obtained for testing may not completely or accurately represent sheet material that has been produced.

To overcome the limitations of laboratory testing, various devices have been proposed for making measurements of properties of traveling webs of fibrous material "on-line", i.e., while a sheet-making machine is operating. On-line measurement devices have been proposed, for example, for measuring properties including basis weight, dry basis weight, moisture content, thickness, and transmissivity. In papermaking processes, however, it has proven difficult to design on-line measuring devices that operate accurately and for extended periods without undue repair and maintenance, and without causing down-time to sheet-making machines. The difficulties arise, in part, because modern papermaking machines are large and operate at high speeds. For example, some conventional papermaking machines are large enough to produce sheets that are 100 to 400 inches wide at rates from about 20 to 100 feet per second. Furthermore, on-line measurements in papermaking processes are often difficult to obtain because the environment around a papermaking machine may include a high concentration of water droplet and airborne chemicals.

Among the on-line measurement devices that have been proposed are sensors that periodically traverse or "scan" traveling webs of sheet material. For example, U.S. Pat. Nos. 3,641,349; 3,681,595; 3,757,122; and 3,886,036 assigned to Measurex Corporation discuss basis weight gauges of the scanning type. Also, U.S. Pat. 4,289,964, assigned to Intec Corporation, suggests that beta ray gauges can scan across a traveling web in the cross direction to determine basis weight.

Despite numerous advantages of scanning gauges in sheet-making operations, many such gauges have encountered problems. Problems have arisen, for example, because moving parts in conventional scanning gauges require relatively frequent repair and maintenance. Also, conventional scanning gauges require relatively long periods to provide a "profile" of a traveling web. (In the sheet-making art, a profile is comprised of a succession of measurements at adjacent locations that, in total, extend completely across a traveling web.) For instance, conventional scanning gauges for detecting basis weight and moisture content of fibrous sheet materials normally require about thirty seconds to obtain a profile of a traveling sheet of average width. Thus, such conventional scanning devices are not well suited for high-speed papermaking machines whose control systems operate optimally when relatively larger numbers of measurements are provided over relatively shorter periods of time.

Specific examples of scanning gauges proposed by workers in the art include ones that detect the composition of sheet material by measuring the radiation absorbed from beams of infrared light or other radiation of known wavelength directed against a given area of the sheet material. That is, such devices operate in accordance with the general principal that the amount of radiation absorbed by sheet material at a particular wave length is a function of the composition of the sheet material; for example, the absorption of infrared light having a wavelength of about 1.5 microns provides an indication of the cellulose content of paper sheet material.

For purposes of on-line scanning of sheets of paper material, however, conventional infrared detectors are not completely satisfactory because they are relatively bulky, require mechanically protective enclosure of "heads", and function reliably only in environments that are cool, dry and of constant temperature. Due to such limitations, conventional infrared detectors are normally used at scanning speeds less than about fifteen inches per second. As mentioned above, such scanning speeds impose limitations upon data acquisition rates and, in turn, impose limitations upon control systems that employ the sensors. For modern high-speed papermaking machines, it can be said that the data acquisition rates reliably obtainable with conventional infrared scanners are too slow for optimum benefits to be derived from computerized control systems.

As further background to the present invention, it is useful to generally describe a typical papermaking process. Generally speaking, a papermaking process begins when a slurry of fibers and water, called raw stock, is spread onto a supporting wire mesh from a reservoir called a head box. The wire mesh supports the fibers while allowing substantial drainage. The web is passed through a press section that squeezes water from the web and then through a dryer section to evaporate water from the web. After the dryer section, the web passes through calendar rollers and, usually, through a scanner and onto a reel.

The portion of a papermaking process prior to the dryer section is often referred to as the "wet end". It can be appreciated that on-line measurements at the wet end are desirable because such measurements, if acted upon promptly, may minimize wastage by indicating needed process changes before substantial quantities of substandard paper are produced. On the other hand, wet end measurements are difficult to make because of the high water content, usually about sixty percent, of paper webs at this stage and because of severe environmental conditions.

OBJECTS AND SUMMARY OF THE PRESENT INVENTION

Generally speaking, an object and advantage of the present invention is to provide an improved method and system employing infrared detectors to measure properties of traveling webs of sheet material.

More particularly, an object of the present invention is to provide an improved system and method employing infrared detectors to rapidly measure properties such as dry basis weight and moisture content at identifiable locations across profiles of traveling webs of sheet material.

In accordance with the preceding objects, the present invention generally provides a system for determining optically-sensitive properties of traveling webs of sheet material during manufacture comprising: a first track mounted to extend generally parallel to one face of a traveling web in the cross direction; a stationary light source arranged to direct collimated light parallel to the first track; a first reflector mounted to travel back and forth along the first track and to focus the collimated light against the adjacent face of the web; a second track mounted to extend generally parallel to the first track adjacent the opposite face of the web; a second reflector mounted to travel back and forth along the second track means to collect rays that are transmitted through the web and to re-collimate and direct the rays to one end of the track; and a stationary array of light detectors to detect the intensity of rays collected by the second reflector at least at two selected ranges of wavelengths to, thereby, provide measurements of the absorption properties of the traveling web at selected locations.

Further, the present invention provides a method for optically determining properties of traveling webs of sheet material. The method includes the steps of providing a modulated beam of collimated light; focusing rays from the collimated beam onto the surface of the traveling web with a first traveling reflector that progressively moves back and forth across the web; collecting rays transmitted through the traveling web with a second traveling reflector that travels in parallel with the first reflector; re-collimating and directing the rays to a stationary detector that detects the intensity of the collected rays; and providing electrical output signals proportional to the intensity of detected light to indicate absorption properties of the traveling web at identifiable locations.

The foregoing and other aspects of the present invention can be readily ascertained by reference to the following description and attached drawings which illustrate the preferred embodiment.

DETAILED DESCRIPTION OF THE PREFERRED EMBODIMENT

Figure 1:
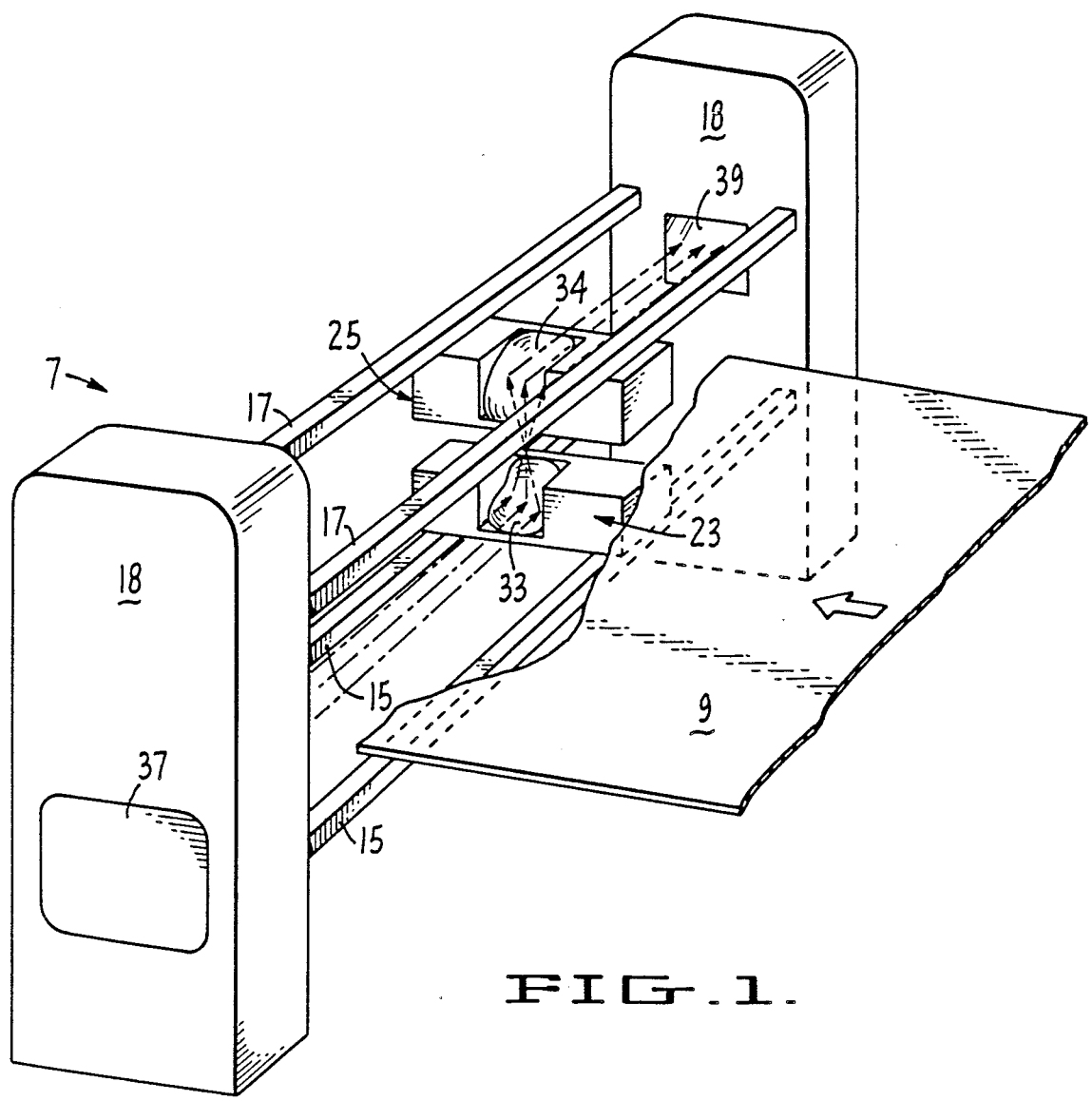
FIG. 1 is a generally schematic pictorial view of a measuring device that operates according to the present invention.

FIG. 1 shows a device, generally indicated by the numeral 7, for providing measurements of a web 9 of sheet material traveling horizontally through the machine in the direction indicated by the arrow. Measuring device 7 is intended for installation on a papermaking machine at any convenient location between a first press section and a windup roll. Measuring device 7 generally includes pairs of horizontally extending guide tracks 15 and 17, respectively, that span the width of web 9 parallel to its opposite faces in the cross-direction. (In the sheet-making art, the direction of sheet travel is known as the "machine direction" and the direction across a sheet that is perpendicular to the machine direction is known as the "cross direction"; depending upon the papermaking machine, the cross direction can range in length from about 100 inches to about 400 inches.) Pairs of guide tracks 15 and 17 are supported at their opposite ends by upstanding stanchions 18 and are spaced apart vertically by a distance sufficient to allow clearance for web 9 to travel between the tracks.

As further shown in FIG. 1, the pairs of guide tracks 15 and 17 support traveling carriage devices 23 and 25, respectively, that carry parabolic mirrors 33 and 34, respectively, to scan web 9. Generally speaking, parabolic mirror 33 has a reflection angle of ninety degrees and is mounted to receive and reflect collimated light from a source 37 to provide rays focused against the surface of web 9. Parabolic mirror 34 also has a reflection angle of ninety degrees and is mounted to collect light that passes through web 9 from mirror 33 and to reflect that light as a collimated beam to a detection assembly 39. Thus, parabolic mirrors 33 and 34 are essentially identical but oppositely oriented. Generally speaking, light detection assembly 39 serves to detect the amount of light from source 37 transmitted through web 9 between mirrors 33 and 34 while the mirrors are traveling in tandem in the cross-direction along guide tracks 15 and 17. In operation, carriage devices 23 and 25 travel progressively across web 9 and are always aligned opposite each other such that parabolic mirror 34 is directly above parabolic mirror 33 regardless of the scanning position of the two mirrors on tracks 15 and 17.

At this juncture, workers skilled in the art will recognize that it is well known to provide scanning devices carried by rails or tracks that span a traveling web. Thus, the particular design and construction of guide tracks 15 and 17 and of carriage devices 23 and 25 are matters of choice. The primary design criterion is that the structure serves to reliably carry parabolic mirrors 33 and 34 back and forth across web at generally uniform velocities substantially in excess of about fifteen inches per second, on average, with minimal vibration.

Other components of measuring device 7 for providing optical measurements of a traveling web of sheet material are only generally indicated in FIG. 1. Those components include, in addition to the traveling pair of parabolic mirrors 33 and 34, the light source 37 mounted stationarily at one end of the guide tracks beyond the edge of web 9 and the light detection assembly 39 mounted stationarily at the opposite end of the guide tracks beyond the edge of web 9.

Figure 2:
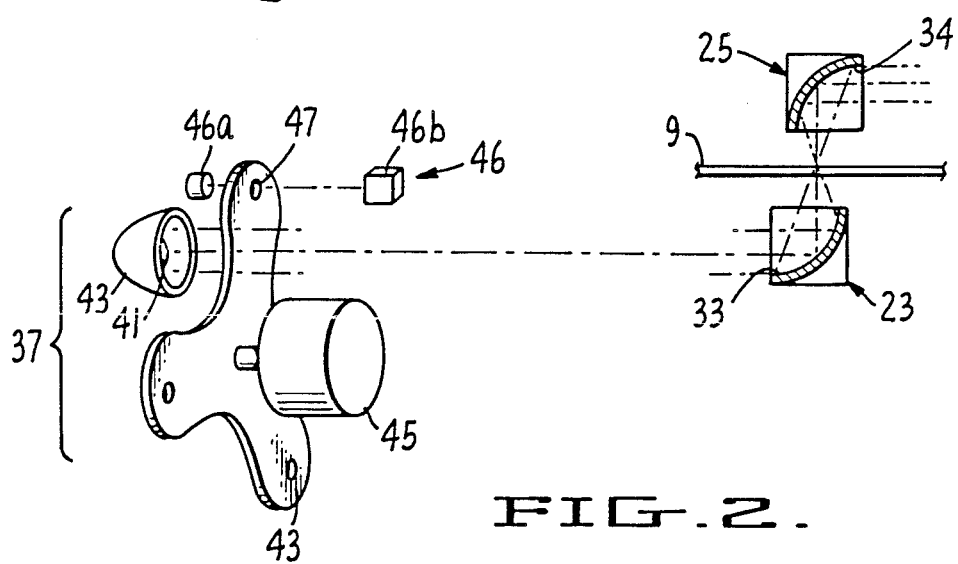
FIG. 2 is a generally schematic diagram of a light source for use with the measuring device of FIG. 1.

In FIG. 2, an assembly comprising an embodiment of light source 37 is shown. In this embodiment, light source 37 includes a conventional incandescent lamp 41 and a parabolic reflector member 3 that collects the radiation from lamp 41 to form a collimated beam of generally parallel rays. Preferably, lamp 41 emits a broad band of visible and infrared radiation including light within the wavelength band between 1.3 and 2.1 microns. Reflector member 43 is arranged to direct the collimated light generally parallel to the surface of web 9 generally in the cross direction.

FIG. 2 further shows a mechanism for modulating, or chopping, the beam of light from source 37. In the illustrated embodiment, the modulating mechanism includes a rotor member 43 having symmetrical vanes that radially extend from its center of rotation. In operation, rotor member 43 is rotatably driven by motor 45 and is positioned such that its vanes alternatively block and unblock the collimated light from lamp 41 depending upon the rotational position of the vanes. A typical chopping rate is about fifty times per second.

As also shown in FIG. 2, a position detector 46 is provided to detect the rotational position of the vanes of rotor member 43. Position detector 46 can be, for example, a light-emitting diode 46a combined with a phototransistor 46b mounted to detect passage of light through apertures 47 in the rotor vanes at predetermined positions. Output signals from position detector 46 are used to provide timing and synchronization as will be later discussed in conjunction with the explanation of FIG. 4.

Figure 3:
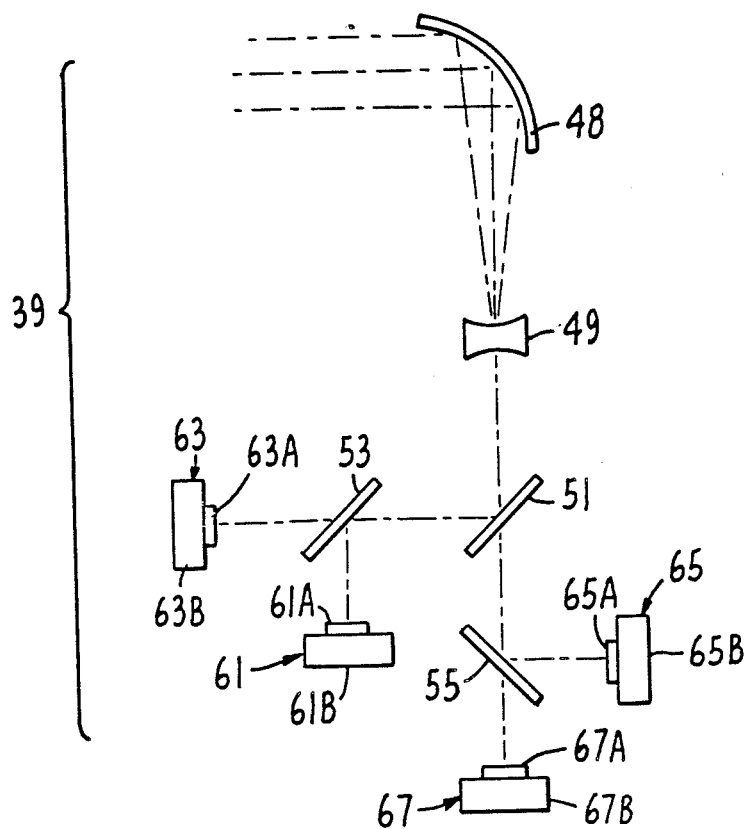
FIG. 3 is a generally schematic diagram of a light detection assembly for use with the measuring device of FIG. 1.

Reference is now be made to FIG. 3 which shows that light detection assembly 39 includes components for collecting, filtering and sensing light rays that have been transmitted through web 9 and collected by traveling mirror 34. In the preferred embodiment, the collecting components include a third parabolic mirror 48 that is stationarily mounted to receive and convergingly focus light reflected from traveling mirror 34, and a lens 49 that is arranged generally at the focal point of mirror 48 to receive and collimate the focused light. In the illustrated embodiment, parabolic mirror 48 has a reflection angle of ninety degrees. A transmitting-reflecting mirror 51, typically referred to as a beam splitting mirror, is arranged in the path of the collimated rays from lens 48. Transmitting-reflecting mirror 51 passes (i.e., transmits) a substantial fraction of the rays that are incident upon its surface and reflects the remainder of the rays. A second transmitting-reflecting mirror 53 is arranged in the path of the rays that are reflected from mirror 51. The second transmitting-reflecting mirror 53 is essentially the same as first transmitting-reflecting mirror 51 and serves to transmit a substantial fraction of the rays incident upon its surface and to reflect the remainder of the rays. The reflected rays from mirror 53 are directed to a first optical detector 61 that filters and senses the rays. A second detector 63 is mounted in the path of the transmitted rays from transmitting-reflecting mirror 53. A third transmitting-reflecting mirror 55 is arranged in the path of the rays transmitted through mirror 51 and, similarly, serves to transmit a fraction of the rays and to reflect a fraction of the rays. A third detector 65 is arranged in the path of the rays reflected from mirror 55, and a fourth detector 67 is arranged in the path of the rays transmitted through mirror 55. The transmitting-reflecting mirrors 51, 53 and 55 are well known as components in optical systems; the arrangement of the transmitting-reflecting mirrors in light detection assembly 39 is a matter of choice depending upon the space available and other mechanical design considerations.

In the embodiment shown in FIG. 3, optical detectors 61, 63, 65 and 67 each include a bandpass filter and a photoelectric transducer. Thus, the bandpass filter associated with detector 61 is designated as 61A and the photoelectric transducer associated with the detector is designated as 61B; likewise, the bandpass filter for detector 63 is designated as 63A, the photoelectric transducer for detector 63 is designated as 63B, and so forth. Bandpass filters 61A, 63A, 65A and 67A differ from each other in terms of the bands of wavelengths of light that they pass. In papermaking operations, where the infrared spectrum is of primary interest, the bandpass filters may be selected as follows: bandpass filter 61A is selected to pass light in a narrow band of wavelengths about a mean value of 1.5 microns, bandpass filter 63A is selected to pass light in a narrow band of wavelengths about a mean value of 1.3 microns, bandpass filter 65A is selected to pass light in a narrow band of wavelengths about a mean value of about 1.9 microns, and bandpass filter 67A is selected to pass light in a narrow band of wavelengths about a mean value of 1.8 microns. For convenience, such values and alternative values are summarized in the table below.

| Bandpass Filters | Wavelength Passed (mean value) |
| --- | --- |
| 61A | 1.5 or 2.1 microns |
| 63A | 1.3 or 1.8 microns |
| 65A | 1.9 microns |
| 67A | 1.8 microns |

In the discussion that follows, the wavelengths of light passed by bandpass filters 61A and 65A will be called the "measurement" wavelengths and the wavelengths passed by bandpass filters 63A and 67A will be called the "reference" wavelengths. In practice, the measurement wavelengths are selected for preferential absorbtion by the sheet material of web 9 and the reference wavelengths are selected for less substantial absorbtion. In papermaking operations, for example, one measurement wavelength is normally chosen for specific absorption by cellulose fibers and one reference wavelength is chosen to be near, but outside, the resonant absorption band of cellulose.

The photoelectric transducers 61B, 63B, 65B and 67B in the light detection assembly 39 in FIG. 3 are substantially identical. The transducers can, for example, be of the type made from lead sulfide. In assembled condition, photoelectric transducers 61B, 63B, 65B and 67B are mounted to respective bandpass filters 61A, 63A, 65A and 67A such that all light reaching the transducers passes through the filters. Thus, in the case where bandpass filters 61A and 65A pass light at the measurement wavelengths, transducers 61B and 65B receive light only at the measurement wavelengths; likewise, in the case where bandpass filters 63A and 67A pass light at the reference wavelengths, transducers 63B and 67B will receive light only at the reference wavelengths. As will become clear from the description below of the operation of light detection assembly 39, the number of light detectors that is provided is a matter of choice depending upon the number of independent measurements that are desired for each area of web 9; as a general rule, however, at least two detectors are provided.

Figure 4:
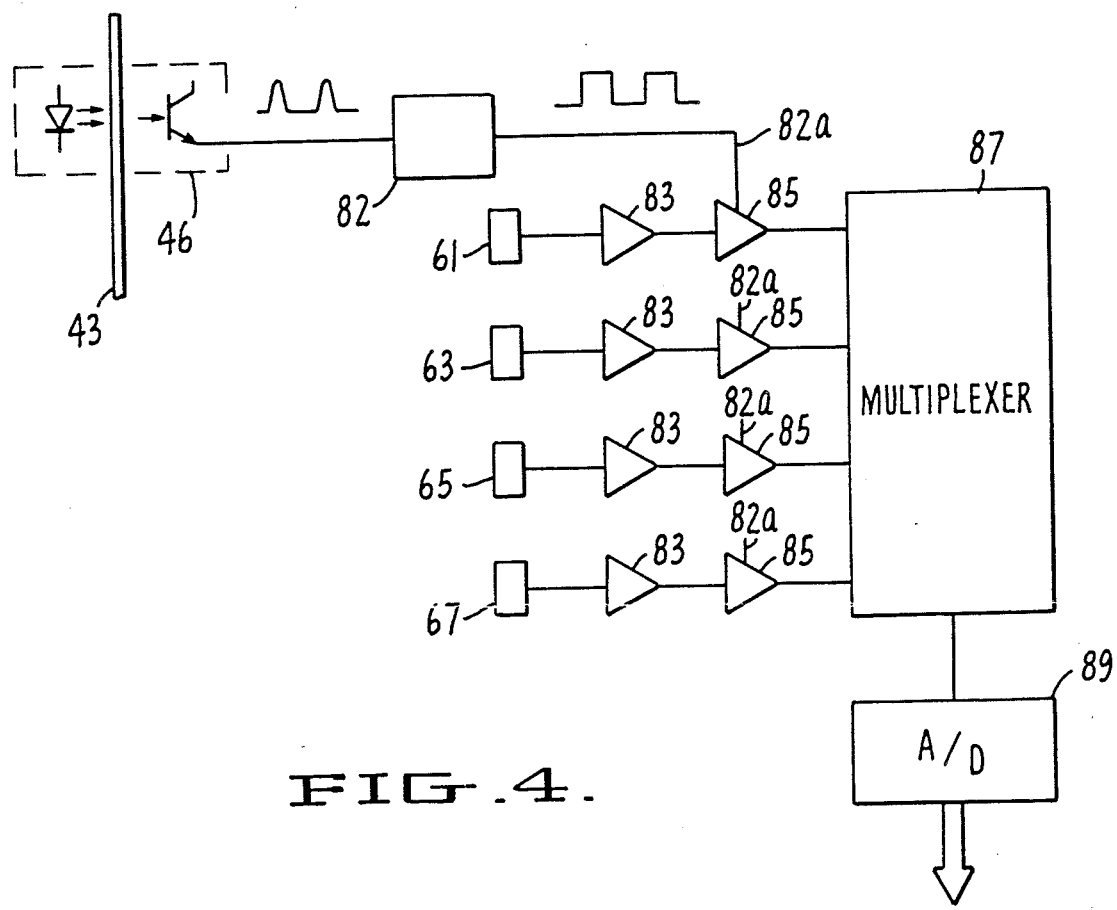
FIG. 4 is a functional diagram of an electronic system for processing signals obtained by the light detection assembly of FIG. 3.

Referring now to FIG. 4, an electronic system is schematically shown for processing electrical signals produced by the light detectors 61, 63, 65 and 67. The purpose of the electronic system is to provide sequential output signals indicative of measured optical properties across profiles of traveling webs based upon the intensity of selected wavelength bands of light measured by light detectors 61, 63, 65 and 67. In the system of FIG. 4, conventional preamplifiers 83 are connected to amplify the electrical output signals from transducers 61, 63, 65 and 67. Further in the system in FIG. 4, position detector 46 provides output signals that are indicative of the rotational position of rotor member 43 of FIG. 2. The output signals from position detector 46 are conveyed to a pulse converter 82 that converts the signals into square-wave output signals that are transmitted, via lines 82a, to demodulators 85 for synchronization purposes. The demodulators 85 are connected to demodulate output signals from preamplifiers 83 to provide direct current signals that have amplitudes proportional to the intensity of light received by respective detectors 61, 63, 65 and 67. As further shown in FIG. 4, demodulated signals derived from detectors 61, 63, 65 and 67 are multiplexed by a multiplexer 87. The multiplexed signals are converted to digital form by a conventional analog-to-digital converter 89 for further processing as by a microprocessor-based computer (not shown). In the system of FIG. 4, the electronic processing components (i.e., pulse converter 82, preamplifiers 83, demodulators 85, multiplexer 87, and analog-to-digital converter 89) are of conventional design and are well known in the signal processing art.

In practice, the system of FIG. 4 will yield a sequence of outputs from analog-to-digital converter 89 that can be correlated with the cross-direction location of each measurement. Identification of cross-direction locations permits precise control of production conditions by, for example, automatically controlling selected slice lip openings at the headbox of a papermaking machine.

Operation of measuring device 7 of FIG. 1 will now be described in the context of providing measurement of parameters such as basis weight, moisture content and dry basis weight. To initiate such measurements, light source 37 is illuminated and rotor member 43 (FIG. 2) is rotatably driven to modulate the collimated light emitted from lamp 41. When the light beam from lamp 41 is not blocked by the vanes of rotor member 43, the beam extends parallel to track member 15 in a position to be incident upon traveling parabolic mirror 33. Parabolic mirror 33 reflects the beam and focuses it against the surface of traveling web 9. Of the rays incident upon the surface of web 9, some will be reflected by the material of the web, some will be absorbed, and many will be transmitted through the web. The rays that pass through web 9 will emerge generally as a diverging cone of rays from the web surface. The cone of emerging rays is collected by traveling parabolic mirror 34 and reflected as a collimated beam of rays directed generally parallel to the surface of web 9. Stationary parabolic mirror 48 (FIG. 3) is arranged at a convenient location beyond the edge of the web to intercept the collimated beam. From parabolic mirror 48, the reflected light rays are directed through lens 49 and then onto transmitting-reflecting mirror 51. From mirror 51, light rays are directed to mirrors 53 and 55 as previously described and ultimately to detectors 61, 63, 65 and 67. Output signals from the detectors can be used to calculate parameters such as the basis weight and moisture content of web 9 as will now be explained.

Generally speaking, the above system can provide measurements of dry basis weight (DBW), basis weight (BW) and percent moisture content (MC) of web 9 are as follows:

$$DBW = f(MES1, MES2, REF1, REF2)$$

$$BW = g(MES1, MES2, REF1, REF2)$$

$$MC = h(MES1, MES2, REF1, REF2)$$

wherein f, g and h are empirical functions.

Signals determined when web 9 is present may be referred to as "on-sheet" signals, and signals determined when web 9 is not present may be referred to as "off-sheet" signals. Thus, in regard to the preceding equations, the MES1 signal can be understood to be the on-sheet signal at the first measurement wavelength divided by the off-sheet signal at the same wavelength. Similarly, the REF1 signal can be understood to be the on-sheet signal level at the first reference wavelength divided by the off-sheet signal level at the same wavelength. Likewise, the MES2 signal may be the on-sheet signal level at the second measurement wavelength divided by the off-sheet signal level at the same wavelength. Finally, the REF2 signal may be the on-sheet signal level at the second reference wavelength divided by the off-sheet signal level at the same wavelength.

As a specific example, the functions f, g and h in the preceding equations can have the following form:

$$DBW = A0 + A1*\ln(MES1) - A2*\ln(REF1) + A3*\ln(MES2) - A4*\ln(REF2).$$

$$BW = B0 + B1*\ln(MES1) - B2*\ln(REF1) + B3*\ln(MES2) - B4*\ln(REF2).$$

$$MC = C0 + C1*\ln(MES1) - C2*\ln(REF1) + C3*\ln(MES2) - C4*\ln(REF2).$$

In the above formulae, the coefficients A0–A4, B0–B4 and C0–C4 are calibration constants and the asterisks indicate multiplication.

Further in regard to the preceding equation, the wavelengths for the MES1 measurement signals are, in practice, typically chosen to be sensitive primarily to the dry basis weight of the paper. The wavelengths of such signals can be a narrow band about a mean value of 1.5 microns, or, alternatively, a narrow band of wavelengths about a mean value of 2.1 microns. The wavelengths for the REF1 measurement signals are typically chosen at a narrow band of wavelengths about a mean value of 1.3 and are used to correct the basis weight measurement for other properties of the paper as well as for extraneous effects due, for example, to optical attenuation due to changes in reflective properties of optical surfaces. Wavelengths for the MES2 measurement signals are typically chosen at a narrow band of wavelengths about a mean value of 1.9 microns and are sensitive primarily to the water content of paper. Wavelengths for the REF2 measurement signals are typically chosen at a narrow band of wavelengths about a mean value of 1.8 microns and, like wavelengths for the REF1 measurement signals, are used to correct for attenuations due to changes in reflective properties of optical surfaces.

As measuring device 7 of FIG. 1 operates, parabolic mirrors 33 and 34 travel back and forth along guide tracks 15 and 17, respectively, to generally continuously scan the surface of web 9. It should be understood that output signals from the system of FIG. 4 are provided for each successive measurement location across the profiles of web 9. The number of measurement locations is a matter of choice depending upon the clocking rate chosen for the system. A typical clocking rate is about fifty milliseconds. Thus, for a web that is two hundred inches wide and a scanning speed of twenty inches per second, a complete profile of measurements will be completed every ten seconds and each profile would include about two hundred (200) identifiable locations.

One result of providing the above-described non-traveling photoelectric detectors is that profiles of web 9 can be obtained relatively more rapidly and reliably than with conventional traveling detectors. The capability to quickly perform profile measurements allows full utilization of computerized control system capabilities and, in turn, permits much shorter machine control cycles than conventional in papermaking operations. Such control cycles are especially important during startups, grade changes and upsets.

Although the present invention has been described with particular reference to the preferred embodiment, such disclosure should not be interpreted as limiting. Alterations and modifications will, no doubt, become apparent to those skilled in the art after having read the preceding disclosure. For example, third parabolic mirror 48 could readily be replaced by other optical components to provide essentially the same function of collecting and focusing rays reflected from traveling mirror 34; such other components could include, for example, sets of converging lenses. As another example, converging lenses may be mounted on each of the band-pass filters 61A, 63A, 65A and 67A to collect and concentrate the light received by the photoelectric transducers 61B, 63B, 65B and 67B associated with the respective filters. In view of such alternatives and others that will occur to skilled workers, the appended claims should be interpreted as covering all of the various alternative embodiments as fall within the true spirit and scope of the present invention.

I claim:

1. A system for measuring optically-sensitive properties relating to the composition of travelling webs of sheet material during manufacture, comprising:
    (a) first track means mounted to extend generally parallel to one face of a travelling web in the cross direction;
    (b) a stationary light source means arranged to direct collimated light, having ranges of wavelengths, parallel to the first track means;
    (c) first parabolic reflector means mounted to travel along the first track means and to focus the collimated light as rays directed directly from the first parabolic reflector means. onto the adjacent face of the web;
    (d) second track means mounted to extend generally parallel to the first track means adjacent the opposite face of the web;
    (e) second parabolic reflector means mounted to travel along the second track means to immediately collect rays that are transmitted through the web from the first parabolic reflector means; and
    (f) stationarily-mounted light detector means to detect rays collected by the second parabolic reflector means at least at two selected ranges of wavelengths to provide measurement of optical absorption properties relating to the composition of the travelling web at selected locations.

2. A system according to claim 1 further including means to modulate light emitted from said light source means.

3. A system according to claim 1 wherein the detector means comprises sets of photoelectric transducers and associated optical filters that each preferentially pass a selected band of wavelengths of light.

4. A system according to claim 3 further including beam splitting means to direct the collected rays to the detector means.

5. A system according to claim 4 wherein said detector means comprises at least two sets of photoelectric transducers and associated optical filters arranged to measure split components of the collected rays.

6. A system according to claim 4 wherein said detector means comprises at least four sets of photoelectric transducers and associated optical filters arranged to measure split components of the collected rays.

7. A system according to claim 1 wherein the detector means includes means to re-collimate the collected rays.

8. A system according to claim 7 wherein the re-collimating means comprises a parabolic mirror to focus the collected rays and a lens mounted to recollimate the focused rays.

9. A system according to claim 1 wherein the first parabolic reflector means comprises a parabolic mirror having a reflection angle of about ninety degrees.

10. A system according to claim 9 wherein the second parabolic reflector means includes a parabolic mirror to collect rays of light transmitted through the web from the first parabolic reflector means.

11. A system according to claim 1 wherein both the first and second parabolic reflector means each comprise parabolic mirror having reflection angles of about ninety degrees.

12. A method for optically measuring optically-sensitive properties relating to the composition of travelling webs of sheet material, comprising the steps of:
    (a) directing at least one beam of collimated light generally parallel to the surface of a travelling web;
    (b) focusing rays from the beam with a first parabolic reflector that travels parallel to one face of the web in the cross direction, said rays being focused directly from the first parabolic reflector onto the adjacent face of the web;
    (c) immediately collecting and collimating one of said focused rays that are transmitted through the web with a second parabolic reflector that travels parallel to the first parabolic reflector adjacent the opposite face of the web;
    (d) detecting the intensity of the collected rays with at least two stationary light detectors that detect the intensity of light at least at two different ranges of wavelengths to measure optical absorption properties relating to the composition of the travelling web at identifiable locations.

13. A method according to claim 12 wherein the detected light is in the near infrared spectrum.

14. A method according to claim 13 wherein the beam of collimated light is modulated.

15. A method according to claim 14 wherein the step of focusing the rays is accomplished with a ninety degree angle of reflection.

16. A method according to claim 13 wherein the steps of collecting and collimating are accomplished with a second parabolic mirror which provides a reflection angle of about ninety degrees.

17. A method according to claim 13 wherein the collected rays are subsequently split and separately directed to means for detecting their intensity.

18. A method according to claim 17 wherein the intensity of the collected rays is measured at least at two distinct narrow bands of wavelengths of light.

19. A method according to claim 17 wherein the intensity of the collected rays is measured at least at three distinct narrow bands of wavelengths of light.

20. A method according to claim 17 wherein the intensity of the collected rays is measured at least at four distinct narrow bands of wavelengths of light.

21. A method according to claim 19 including the step of computing parameters including dry basis weight, basis weight and moisture content of a traveling web by computing values for the following functions:

$$DBW = f(MES1, MES2, REF1, REF2).$$

$$BW = g(MES1, MES2, REF1, REF2).$$

$$MC = h(MES1, MES2, REF1, REF2).$$

wherein
- DBW is dry basis weight of a measured area of the web of sheet material;
- BW is the basis weight of a measured area of the web of sheet material;
- MC is the moisture content of a measured area of the web of sheet material;
- f, g and h are empirical functions;
- MES1 is the detected intensity at a first wavelength band;
- REF1 is detected intensity at a second wavelength band;
- MES2 is detected intensity at a third wavelength band; and
- REF2 is detected intensity at a fourth wavelength band.

22. A method according to claim 21 wherein MES1 is the signal level at the first wavelength band when a web is present divided by the signal level when no web is present, REF1 is the signal level at the second wavelength band when a web is present divided by the signal level when no web is present, MES2 is the signal level at the third wavelength band when a web is present divided by the signal level when no web is present, and REF2 is the signal level at the fourth wavelength band when a web is present divided by the signal level when no web is present.

23. A method according to claim 22 wherein the wavelength band for MES1 is a narrow band of wavelengths around a mean value of 1.5 microns; the wavelength band for REF1 is a narrow band of wavelengths around a mean value of 1.3 microns; the wavelength band for MES2 is a narrow band of wavelengths around a mean value of 1.9 microns; and the wavelength band for REF2 is a narrow band of wavelengths around a mean value of 1.8 microns.

* * * * *

UNITED STATES PATENT AND TRADEMARK OFFICE
CERTIFICATE OF CORRECTION

PATENT NO. : 4,879,471

DATED : November 7, 1989

INVENTOR(S) : John A. Dahlquist

It is certified that error appears in the above-identified patent and that said Letters Patent is hereby corrected as shown below:

Column 1, line 60, "droplet" should read -- droplets --;

Column 4, line 59, "across web" should read -- across a web --;

Column 5, line 6, "member 3" should read -- member 43 --;

Column 8, line 18, ""of-sheet"" should read -- "off-sheet" --;

approximately line 38, "B1*1..." should read --B1*ln...--;

Column 8, line 39, delete "n".

Column 9, line 58, "means. onto" should read -- means onto --;

Column 10, line 2, "measurement" should read -- measurements --;

line 28, "recollimate" should read -- re-collimate --;

line 39, "mirror" should read -- mirrors --;

line 51, "one" should read -- ones --;

line 67, after "a" insert -- first parabolic mirror which provides about --; and

UNITED STATES PATENT AND TRADEMARK OFFICE
CERTIFICATE OF CORRECTION

PATENT NO. : 4,879,471

DATED : November 7, 1989

INVENTOR(S) : John A. Dahlquist

It is certified that error appears in the above-identified patent and that said Letters Patent is hereby corrected as shown below:

Column 11, line 28, "wherein" should read --wherein:--.

Signed and Sealed this

Fifth Day of November, 1991

*Attest:*

HARRY F. MANBECK, JR.

*Attesting Officer*

*Commissioner of Patents and Trademarks*